US00PP31028P3

(12) United States Plant Patent
Szczésny

(10) Patent No.: US PP31,028 P3
(45) Date of Patent: Nov. 5, 2019

(54) ***AJUGA* PLANT NAMED 'PIOTREK01'**

(50) Latin Name: *Ajuga tenorii*
Varietal Denomination: Piotrek01

(71) Applicant: Piotr Szczésny, Waddinxveen (NL)

(72) Inventor: Piotr Szczésny, Waddinxveen (NL)

( * ) Notice: Subject to any disclaimer, the term of this patent is extended or adjusted under 35 U.S.C. 154(b) by 57 days.

(21) Appl. No.: 15/932,127

(22) Filed: Feb. 7, 2018

(65) Prior Publication Data

US 2019/0069464 P1 Feb. 28, 2019

(30) Foreign Application Priority Data

Aug. 30, 2017 (QZ) ..... PBR 20172117

(51) Int. Cl.
*A01H 5/02* (2018.01)
*A01H 6/00* (2018.01)
*A01H 6/50* (2018.01)

(52) U.S. Cl.
USPC ..... Plt./401
CPC ..... *A01H 6/00* (2018.05); *A01H 5/02* (2013.01); *A01H 6/50* (2018.05)

(58) Field of Classification Search
USPC ..... Plt./401
See application file for complete search history.

*Primary Examiner* — Anne Marie Grunberg
(74) *Attorney, Agent, or Firm* — Penny J. Aguirre

(57) ABSTRACT

A new cultivar of *Ajuga* plant, 'Piotrek01', characterized by its abundant blooming habit, its leaves that are small in size, its intense purple flower color, its new shoots that are bright pink in color and its low maintenance plant habit.

2 Drawing Sheets

Botanical classification: *Ajuga tenorii.*
Variety denomination: 'Piotrek01'.

BACKGROUND OF THE INVENTION

The present invention relates to a new and distinct cultivar of *Ajuga tenorii* and will be referred to hereafter by its cultivar name, 'Piotrek01'. 'Piotrek01' represents a new cultivar of *Ajuga*, an herbaceous perennial grown for landscape use.

'Piotrek01' was discovered by the Inventor in 2013 as a naturally occurring meristematic mutation of *Ajuga tenorii* 'Chocolate Chip' (not patented) growing outdoors in a container in Waddinxveen, The Netherlands.

Asexual propagation of the new cultivar was first accomplished by the Inventor by stem cuttings in Waddinxveen, The Netherlands in February of 2017. Asexual propagation by stem cuttings and tissue culture using meristem tissue has shown that the characteristics of the new cultivar are stable and are reproduced true to type in successive generations.

SUMMARY OF THE INVENTION

The following traits have been repeatedly observed and are determined to be the characteristics of the new cultivar. These attributes in combination distinguish 'Piotrek01' as a unique cultivar of *Ajuga.*

1. 'Piotrek01' exhibits an abundant blooming habit.
2. 'Piotrek01' exhibits leaves that are small in size.
3. 'Piotrek01' exhibits an intense purple flower color.
4. 'Piotrek01' exhibits new shoots that are bright pink in color.
5. 'Piotrek01' exhibits low maintenance plant habit.

The parent plant of 'Piotrek01', 'Chocolate Chip', differs from 'Piotrek01' in having non-variegated foliage, leaves that are larger in size and a less dense plant habit. 'Piotrek01' can be most closely compared to *Ajuga* 'Burgundy Glow' (not patented). 'Burgundy Glow' differs from 'Piotrek01' in having leaves that are larger in size, flowers that are lighter purple in color and new shoots that are lighter pink in color and in being less floriferous.

BRIEF DESCRIPTION OF THE DRAWINGS

The accompanying colored photographs illustrate the overall appearance and distinct characteristics of a 1.5 year-old plant the new *Ajuga* as grown outdoors in a 2-liter container in Waddinxveen, The Netherlands.

The photograph in FIG. 1 illustrates the plant habit and floriferous blooming habit of 'Piotrek01'.

Figure 1:
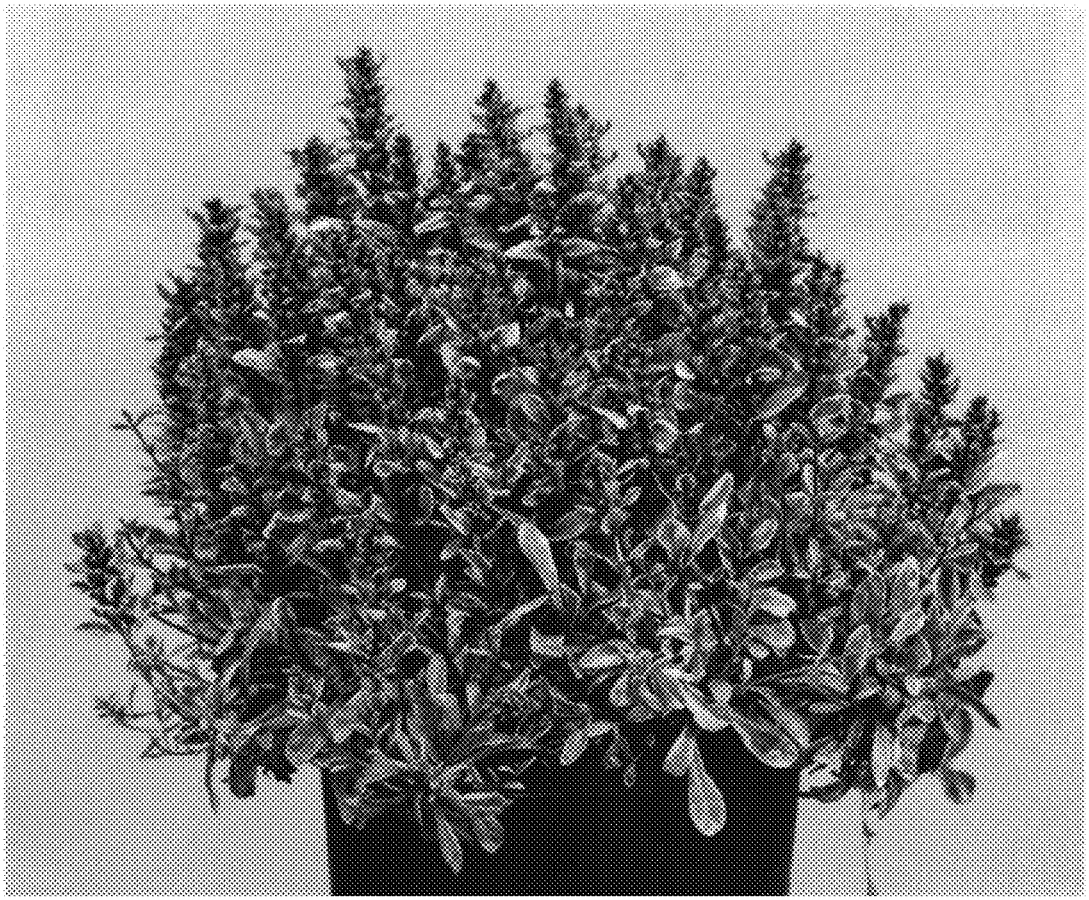
Figure 2:
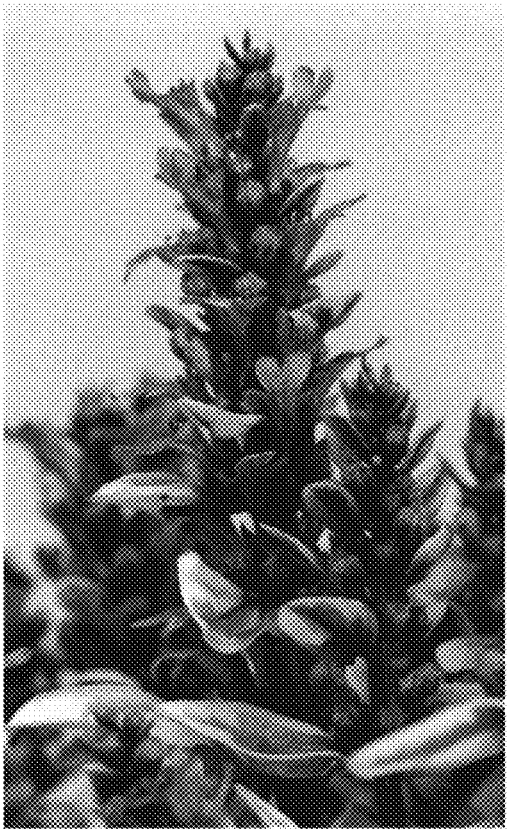

The photograph in FIG. 2 provides a close-up view of an inflorescence of 'Piotrek01'.

Figure 3:
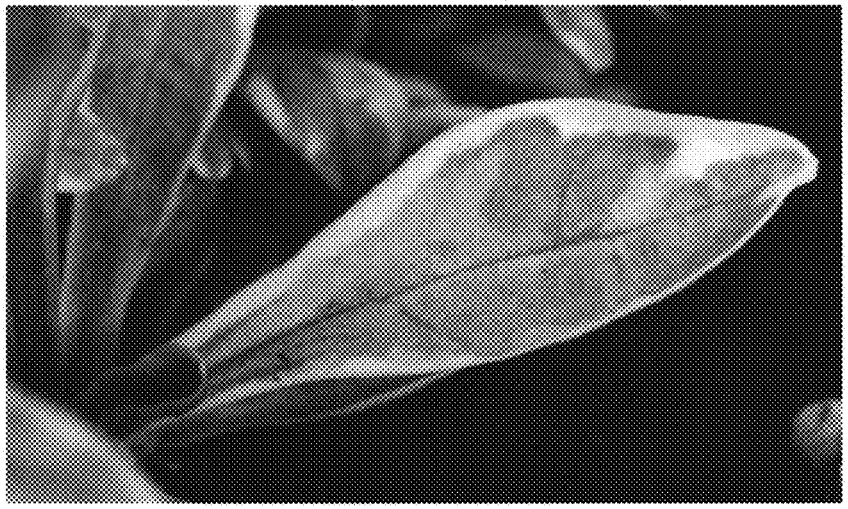

The photograph in FIG. 3 provides a close-up view of the foliage of 'Piotrek01'.

The colors in the photograph may differ slightly from the color values cited in the detailed botanical description, which accurately describe the colors of the new *Ajuga.*

DETAILED BOTANICAL DESCRIPTION

The following is a detailed description of the new cultivar as observed on 1.5 year-old plants as grown outdoors in 2-liter containers in in Waddinxveen, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—Mid March to May and re-blooming with fewer inflorescences in summer in The Netherlands.

*Plant type.*—Herbaceous perennial.

*Plant habit*.—Broadly spreading, compact upright inflorescences.

*Height and spread*.—10 to 15 cm in height (soil level to top of foliar plane), an average of 20 cm in height (soil level to top of floral plane) and 25 cm in width.

*Cold hardiness*.—At least in U.S.D.A. Zones 4 to 10.

*Diseases and pests*.—No susceptibility or resistance to diseases or pests has been observed.

*Root description*.—Fine and fibrous.

*Propagation type*.—Stem cuttings and issue culture.

*Root development*.—Rooted stem cuttings will fully root in a 2-liter container in 6 to 8 weeks.

*Growth rate*.—Moderate.

Stem description:

*Stem shape*.—Quadrangular.

*Stem color*.—Young; 197A, mature; 144A, internodes; 144A to 144B.

*Stem size*.—An average of 8.4 cm in length and 2 mm in diameter.

*Stem surface*.—Glossy, sparsely covered with very short hairs; average of 0.5 mm in length, too small to measure color.

*Stem aspect*.—Main stems held in an average angle of 15° and lateral stems held at an average angle of 40° to main branch.

*Internode length*.—An average of 2.7 cm.

*Branching habit*.—An average of 72 main basal stems and 4 lateral branches per main stem, moderately strong.

Foliage description:

*Leaf shape*.—Obovate to narrow spathulate.

*Leaf division*.—Simple.

*Leaf base*.—Narrow cuneate.

*Leaf apex*.—Obtuse.

*Leaf venation*.—Pinnate, upper surface color 147A, lower surface color 144A.

*Leaf margins*.—Entire.

*Leaf arrangement*.—Opposite.

*Leaf surface*.—Smooth, glabrous, matte.

*Leaf color*.—New growth upper surface; 138B, irregularly blotched 147A, margins 186D, new growth lower surface; between 138B and 147C, irregularly blotched 13B, leaf margins 186D, mature upper surface; between 138B and 148B, margins 8D, mature lower surface a color between 138A and 138B, margins 4D to slightly lighter.

*Leaf size*.—Average of 3.6 cm in length, 1.1 cm in width.

*Leaf quantity*.—Average of 15 per lateral stem.

*Leaf attachment*.—Sessile.

Flower description:

*Inflorescence type*.—Raceme, individual flowers in clusters of 5 flowers in leaf-axils.

*Inflorescence size*.—An average of 7.6 cm in height and 2.6 cm in width.

*Inflorescence number*.—An average of 72.

*Lastingness of inflorescence*.—Average of 10 days, self-cleaning.

*Flower type*.—Labiate.

*Flower number*.—Average of 35 per inflorescence, 2,500 per plant.

*Flower fragrance*.—None.

*Flower buds*.—Oblanceolate in shape, average of 7 mm in length and 2 mm in diameter, color; 93C, fading lighter towards the base, immature calyx 86C, surface matte and densely covered with short hairs; an average of 0.4 mm in length and 156D in color.

*Flower size*.—Average of 6 mm in height, 7 mm in diameter and 1.1 cm in length, throat diameter 2 mm, tube 6 mm in length and 1.5 mm in diameter.

*Peduncles*.—An average of 6.4 cm in length, 1.75 mm in diameter, held straight on top of lateral branch, moderately strong, color; between N77A and N77C, surface is glossy and sparsely covered with very short hairs; an average of 0.5 mm in length, too small to measure color.

*Pedicels*.—An average of 4 mm in length, 1 mm in diameter, held in an average angle of 40° from peduncle, moderately strong, 144A in color, surface is moderately glossy and sparsely covered with very short hairs an average of 0.3 mm in length, too small to measure color.

*Calyx*.—Rotate and tubular in shape, 3.5 mm in length, 4 mm in diameter.

*Sepals*.—5, 1 whorl, average of 4 mm in length, 1.5 mm in width, ovate in shape, 25% of base fused into tube, acute apex, entire margins, color; when opening and fully opr upper surface 91A, when opening lower surface 86C, when fully open lower surface 90D, texture upper and lower surface smooth and glabrous with margins moderately pubescent with very short hairs; an average of 0.3 mm in length and 156D in color.

*Petals*.—Average of 5, 1 whorl, 55% of petals fused into tube, upper petals; average of 9 mm in length, 2 mm in width, oblanceolate in shape, obtuse apex, entire margins, no undulation, upper and lower surface moderately covered with very short hairs; an average of 0.4 mm in length and 156D in color, lower petals; average of 1.1 cm in length, 4 mm in width, oblanceolate in shape, apex is obtuse with lower petal cleft 2-lobed, entire margins, no undulation, upper and lower surface moderately covered with very short hairs; an average of 0.4 mm in length and 156D in color, flower throat texture is smooth and glabrous, flower tube texture upper (inner) side is smooth and glabrous, flower tube texture outer side is moderately pubescent with very short hairs; an average of 0.4 mm in length and 156D in color, color all petals; when opening and fully open upper surface a color between N88A and N88B with veins on upper surface N88A, when opening lower surface 83B, when fully open lower surface 93B, flower throat between N88A and N88B, flower tube 93B on inner and outer surface.

Reproductive organs:

*Pistils*.—1, style; 7.5 mm in length, 90D in color, stigma; 0.2 mm in length, cleft in shape, ovary; 143B in color.

*Stamens*.—4, filament; implanted into flower tube, two filaments longer, two are shorter, average length of short filaments is 1 mm, average length of longer filaments is 2 mm, 93C in color, anthers; dorsifixed, narrow elliptic in shape, 1 mm in length, 0.5 mm in width and 202A in color, pollen; moderate in quantity and 5C in color.

*Fruit*.—Fruit and seed production has not been observed to date.

It is claimed:

1. A new and distinct variety of *Ajuga* plant named 'Piotrek01' as described and illustrated herein.

* * * * *